March 5, 1940. C. C. MAYHEW Plant Pat. 368
YELLOW CHRYSANTHEMUM PLANT
Filed Dec. 10, 1938
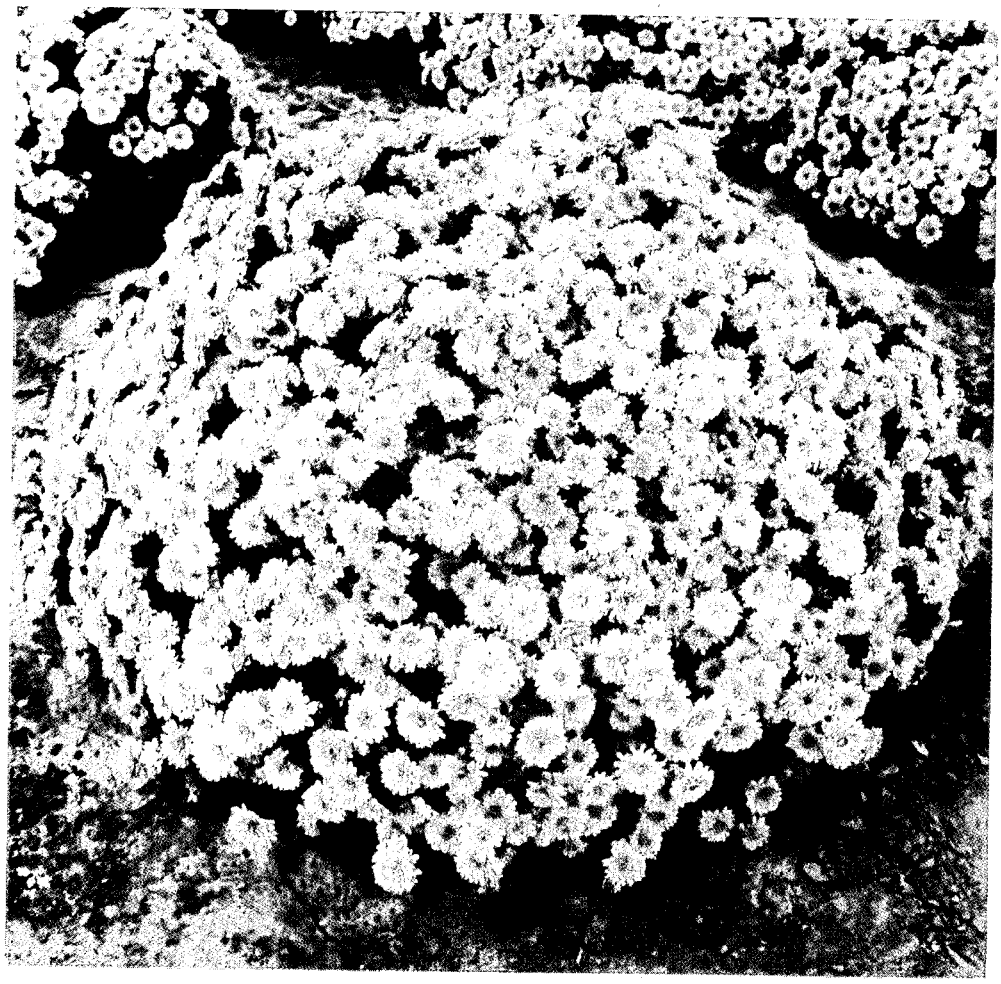
Inventor:
Clarence C. Mayhew
By Robert Robb
Attorney Patented Mar. 5, 1940

Plant Pat. 368

UNITED STATES PATENT OFFICE

368

YELLOW CHRYSANTHEMUM PLANT

Clarence C. Mayhew, Sherman, Tex., assignor to
Texas Nursery Company, Sherman, Tex.

Application December 10, 1938, Serial No. 245,043

1 Claim. (Cl. 47—60)

This invention relates to a novel and distinct variety of chrysanthemum plant of a type whose blossoms grow many to the stem, and in such a manner as to give a spheroidal or mound-like appearance to the blooming plant, which presents flowers all over its outer surface.

The characteristics of my new variety make it a very desirable plant for use in group or border planting. The plant is dwarf in type and compact in habit of growth, ordinarily attaining a height of from fifteen to eighteen inches in the region of Texas. It is particularly distinguished by the yellow color of its flower.

My new variety of chrysanthemum originated as a sport from the variety of chrysanthemum shown and described in Plant Letters Patent No. 204, issued on November 17th, 1936, and was discovered as a branch growing on its parent plant, and is identical with its parent variety in substantially all characteristics of form, habit and growth, including its many flowered characteristic and the tendency of the plant to grow in such a manner as to give it a spheroidal or mound-like appearance.

The shape of the blooms of my new variety is also similar to that of the parent variety, the blooms of both being of rounded form and having petals arranged in a double row. However, the outstanding distinguishing feature between the two varieties lies in the color of their respective flowers. The color of the blooms of my new variety is yellow in general appearance, while the blooms of the variety of Plant Letters Patent No. 204 are white.

My new variety of chrysanthemum and the variety from which it sported both differ from other varieties of chrysanthemums in regard to their blooming period. The variety herein described and the variety of Plant Letters Patent No. 204 bloom two to three weeks earlier than other varieties of chrysanthemums in the region of Texas. My new variety ordinarily begins to bloom about the first of May and the blooming period continues until about the first of December, in this region. The peak of the blooming period is usually reached from about the middle of October to the middle of November.

My new variety of chrysanthemum has been asexually reproduced, propagation being carried on from cuttings, and has been found to hold its distinguishing characteristics through succeeding generations.

The following is a detailed description of my new variety of chrysanthemum:

Plant:
Mound-like in form.
Flower:
Many to a stem, of rounded form.
Stem:
Strong, rather short.
Quality of bloom:
Abundant—outdoors.
Continuity:
Continuous from May to December.
Fragrance:
Moderate, spicy.
Bloom:
When fully open is medium, one and one-half inches to two inches across.
Petalage:
Double, arranged regularly.
Color:
Compared with Ridgway's Chart:
*Buds.*—Lemon Chrome (Plate IV).
*Flowers.*—Open with center petals Lemon Chrome (Plate IV) blending from center to outer petals through tones of Pinard Yellow, Baryta Yellow to Maize Yellow (Plate IV) at the outside. In the open flower the backs of petals have tones of Alizarine Pink and Chatenay Pink (Plate XIII). In older flowers these colors fade to less intense tones of the same hues. All stages on plant at one time. (Description of flowers made from newly opened flowers grown outdoors.)
Foliage:
Moderate, dark green.
Growth:
Dwarf, spreading, much branched.

I claim:

A new and distinct variety of chrysanthemum plant, substantially as herein shown and described, characterized by the yellow color of its flower.

CLARENCE C. MAYHEW.